United States Patent
Guillet et al.

(10) Patent No.: US 8,841,493 B2
(45) Date of Patent: Sep. 23, 2014

(54) PROCESS FOR PREPARING FLUOROOLEFIN COMPOUNDS

(75) Inventors: Dominique Guillet, Vernaison (FR); Michel Devic, Sainte Foy les Lyon (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/375,582

(22) PCT Filed: May 4, 2010

(86) PCT No.: PCT/FR2010/050847
§ 371 (c)(1),
(2), (4) Date: Dec. 16, 2011

(87) PCT Pub. No.: WO2010/139873
PCT Pub. Date: Dec. 9, 2010

(65) Prior Publication Data
US 2012/0083632 A1   Apr. 5, 2012

(30) Foreign Application Priority Data
Jun. 4, 2009   (FR) ...................................... 09 53701

(51) Int. Cl.
*C07C 17/25*   (2006.01)
*C07C 21/18*   (2006.01)

(52) U.S. Cl.
USPC ........... 570/155; 570/157; 570/204; 570/226; 570/227

(58) Field of Classification Search
USPC .................................. 570/155, 157, 226, 227
See application file for complete search history.

(56) References Cited

U.S. PATENT DOCUMENTS

| | | | |
|---|---|---|---|
| 2,404,538 A * | 7/1946 | Schmerling et al. | 585/436 |
| 3,499,048 A | 3/1970 | Regan | |
| 3,579,595 A | 5/1971 | Regan | |
| 6,124,510 A | 9/2000 | Elsheikh et al. | |
| 6,548,719 B1 | 4/2003 | Nair et al. | |
| 2007/0096051 A1 * | 5/2007 | Nappa et al. | 252/2 |
| 2010/0145111 A1 | 6/2010 | Sharratt et al. | |

FOREIGN PATENT DOCUMENTS

| | | |
|---|---|---|
| WO | WO2007/056194 | 5/2007 |
| WO | WO 2008/030440 | 3/2008 |
| WO | WO 2008075017 A2 * | 6/2008 |

OTHER PUBLICATIONS

Miller, R. D. et. al. (Book Title: Anesthesia, Ebook 2005 page link for the topic "Chemistry of Absorbents": http://www.noranaes.org/logbook/resources/Ebooks/Miller1/Miller%20-%20Anesthesia%206th%20Ed/das/book/body/0/1255/242.html#top).*
Kaunyants, I.L., et al., Reactions of Fluoro Olefins Communications 13. Catalytic Hydrogenation of Perfluoro Olefins, Institute of Heterootganic Compounds, Academy of Sciences of the USSR, No. 8, Aug. 1960, pp. 1412-1418.
Sianesj, D., et al., Fluoroolefine-Nota 1, eis e trans 1,2,3,3,3-pentafluoroprolilene, Annali di Chimiea, Societa Chimica Italiana, vol. 55, Nos. 8-9, Jan. 1965, pp. 850-861.

* cited by examiner

*Primary Examiner* — Jafar Parsa
*Assistant Examiner* — Medhanit Bahta
(74) *Attorney, Agent, or Firm* — Brinks Gilson & Lione

(57) ABSTRACT

The subject matter of the invention is a process for preparing fluoroolefin compounds. The invention relates more particularly to a process for producing a (hydro)fluoroolefin compound, which comprises (i) bringing at least one compound comprising from three to six carbon atoms, at least two fluorine atoms and at least one hydrogen atom, on the condition that at least one hydrogen atom and one fluorine atom are located on adjacent carbon atoms, into contact with a solid reactant comprising calcium hydroxide.

10 Claims, No Drawings

PROCESS FOR PREPARING FLUOROOLEFIN COMPOUNDS

FIELD OF THE INVENTION

A subject matter of the invention is a process for the preparation of fluoroolefin compounds. The invention relates more particularly to a process for the preparation of hydrofluoropropenes.

TECHNOLOGICAL BACKGROUND

Hydrofluorocarbons (HFCs) and in particular hydrofluoroolefins (HFOs), such as 2,3,3,3-tetrafluoro-1-propene (HFO-1234yf), are compounds known for their properties of refrigerants and heat-exchange fluids, extinguishers, propellants, foaming agents, blowing agents, gaseous dielectrics, monomer or polymerization medium, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

1,2,3,3,3-Pentafluoropropene (HFO-1225ye) is a synthetic intermediate in the manufacture of 2,3,3,3-tetrafluoro-1-propene (HFO-1234yf).

The majority of the processes for the manufacture of hydrofluoroolefins involve a dehydrohalogenation reaction. Thus, the document WO 03/027051 describes a process for the manufacture of fluoroolefins of formula $CF_3CY\!=\!CX_nH_p$, in which X and Y each represent a hydrogen atom or a halogen atom chosen from fluorine, chlorine, bromine or iodine and n and p are integers and can independently take the value zero, 1 or 2, provided that (n+p)=2, which comprises bringing a compound of formula $CF_3C(R^1_aR^2_b)C(R^3_cR^4_d)$, with $R^1$, $R^2$, $R^3$ and $R^4$ independently representing a hydrogen atom or a halogen atom chosen from fluorine, chlorine, bromine or iodine, provided that at least one of $R^1$, $R^2$, $R^3$ and $R^4$ is a halogen atom and that at least one hydrogen atom and one halogen atom are situated on adjacent carbon atoms, a and b being able independently to take the value zero, 1 or 2, provided that (a+b)=2, and c and d being able independently to take the value zero, 1, 2 or 3, provided that (c+d)=3, into contact with at least one alkali metal hydroxide in the presence of a phase transfer catalyst.

This document teaches, in example 2, that, in the absence of a phase transfer catalyst, there is no reaction when 1,1,1,3,3-pentafluoropropane (HFC-245fa) is brought into contact with a 50% by weight aqueous potassium hydroxide (KOH) solution at ambient temperature and under pressure for 24 hours.

In addition, this document suggests a reaction temperature of between −20° C. and 80° C. but does not recommend the use of alkaline earth metal hydroxides due to their limited solubility in water.

The document WO 2008/075017 discloses a dehydrohalogenation process which comprises bringing a hydro(halo)fluoroalkane into contact with a base, optionally in the presence of a solvent. It teaches that, in the absence of a solvent, the hydro(halo)fluoroalkane can be sent over the base under hot conditions or in the molten state.

This document illustrates the dehydrofluorination reaction of 1,1,1,2,3,3-hexafluoropropane (HFC-236ea) to give 1,2,3,3,3-pentafluoropropene (HFO-1225ye) at 150° C. in the presence of a 50% by weight aqueous KOH solution. In the absence of a phase transfer catalyst, the conversion after 3 and a half hours is 57.8% and the selectivity for HFO-1225ye is 52.4% (test 1). In the presence of a phase transfer catalyst, this conversion is achieved after only 2.5 hours and the selectivity is virtually unchanged (test 4). As indicated in table 2 of this document, it is necessary to use an organic solvent in order to increase the selectivity for HFO-1225ye.

WO 2007/056194 describes the preparation of HFO-1234yf by dehydrofluorination of 1,1,1,2,3-pentafluoropropane (HFC-245eb) either with an aqueous KOH solution or in the gas phase in the presence of a catalyst, in particular over a catalyst based on nickel, carbon or a combination of these.

A description is given, in the document WO 2008/030440, of an embodiment for the dehydrofluorination of 1,1,1,2,3-pentafluoropropane using a basic aqueous solution in the presence of a nonaqueous and non-alcoholic solvent in which the HFC-245eb is partially miscible.

The document Knunyants et al., Journal of the USSR Academy of Sciences, Chemistry Department, "Reactions of fluoro-olefins", Report 13, "Catalytic hydrogenation of perfluoro-olefins", 1960, clearly describes various chemical reactions on fluorinated compounds. This document describes the dehydrofluorination of 1,1,1,2,3,3-hexafluoropropane (236ea) by passing through a suspension of KOH powder in dibutyl ether, to produce 1,2,3,3,3-pentafluoro-1-propene (HFO-1225ye) with a yield of only 60%. This document also describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether with a yield of only 70%.

Finally, the paper by Sianèsi Dario et al. in Annali di Chimica, Societa Chimica Italiana, Rome, Italy, vol. 55, nos. 8-9, 1 Jan. 1965, pages 850-861, describes the dehydrofluorination of 1,1,1,2,3,3-hexafluoropropane using KOH.

The dehydrofluorination reactions as described above result, in addition to the desired hydrofluoroolefin compound, in the formation of water and potassium fluoride. Furthermore, the implementation of such a reaction continuously is not easy on an industrial scale as at least three phases (gas, liquid and solid) are involved and the removal of the potassium fluoride formed in a stoichiometric amount presents a problem.

The present invention provides a process for the continuous or semicontinuous manufacture of a (hydro)-fluoroolefin compound which makes it possible to overcome the abovementioned disadvantages. The reaction involved in the process is a gas/solid reaction.

A subject matter of the present invention is thus a process for the continuous or semicontinuous manufacture of a (hydro)fluoroolefin compound, comprising (i) bringing at least one compound comprising from 2 to 6 carbon atoms, at least two fluorine atoms and at least one hydrogen atom, provided that at least one hydrogen atom and one fluorine atom are situated on adjacent carbon atoms, into contact with a solid reactant comprising calcium hydroxide with coformation of calcium fluoride, a product which can be recovered in value.

The process according to the present invention preferably provides a (hydro)fluoroolefin compound comprising three carbon atoms, advantageously a (hydro)fluoroolefin compound represented by the formula (I)

$$CF_3CY\!=\!CX_nH_p \qquad (I)$$

in which Y represents a hydrogen or halogen atom chosen from fluorine, chlorine, bromine or iodine and X represents a halogen atom chosen from fluorine, chlorine, bromine or iodine; and n and p are integers and can independently take the value zero, 1 or 2, provided that (n+p)=2, by bringing a compound of formula $CF_3CYRCR'X_nH_p$, in which X, Y, n and p have the same meanings as in the formula (I) and R represents a fluorine atom when R' represents a hydrogen atom or R represents a hydrogen atom when R' represents a fluorine atom, into contact with a solid reactant comprising calcium hydroxide.

The present invention is very particularly suitable for the manufacture of a compound of formula (Ia)

$$CF_3-CF=CHZ \qquad (Ia)$$

in which Z represents a hydrogen or fluorine atom, from a compound of formula $CF_3CFRCHR'Z$, in which Z has the same meaning as in the formula (Ia) and R represents a fluorine atom when R' represents a hydrogen atom or R represents a hydrogen atom when R' represents a fluorine atom.

Thus, 2,3,3,3-tetrafluoropropene can be obtained by dehydrofluorination of 1,2,3,3,3-pentafluoropropane with a solid reactant comprising calcium hydroxide and/or 1,2,3,3,3-pentafluoropropene can be obtained by dehydrofluorination of 1,1,1,2,3,3-hexafluoropropane with a solid reactant comprising calcium hydroxide. The 1,2,3,3,3-pentafluoropropene can be in the cis and/or trans isomer form.

The present invention can in addition be used for the manufacture of 1,3,3,3-tetrafluoropropene by dehydrofluorination of 1,1,3,3,3-pentafluoropropane with a solid reactant comprising calcium hydroxide.

In the process according to the present invention, the solid reactant can comprise essentially calcium hydroxide or can comprise predominantly calcium hydroxide and other metal hydroxides, such as NaOH, KOH, $Mg(OH)_2$ and $Ba(OH)_2$.

Use may advantageously be made, as solid reactant, of soda lime, which is calcium hydroxide comprising a few percent by weight of NaOH and KOH.

The KOH content of the solid reactant is preferably between 0.1 and 5% by weight and advantageously between 2 and 4% by weight.

The NaOH content of the solid reactant is preferably between 0.1 and 5% by weight and advantageously between 1 and 3% by weight.

The solid reactant, comprising calcium hydroxide, can be used in the powder form or preferably in the granule form advantageously exhibiting a high porosity. A granule particle size of between 1 and 10 mm is preferred.

The moisture content of the solid reactant is preferably between 1 and 20% by weight, advantageously between 7 and 20% by weight and more particularly between 10 and 15% by weight.

Mention may be made, as example of solid reactant, of soda lime, in particular that sold by Grace under the Sodasorb HP brand.

The process according to the present invention is preferably carried out at a temperature of between 100 and 170° C., advantageously of between 120 and 150° C. A temperature of between 130 and 140° C. is particularly preferred. The dehydrofluorination reaction according to the process of the present invention can be carried out at atmospheric pressure but it is preferable to operate at a pressure in excess of atmospheric pressure, for example between 1 and 10 bar absolute. Advantageously, this pressure is between 5 and 10 bar absolute.

The reaction can be carried out according to the normal means used industrially to carry out a reaction between a gas and a solid, such as, for example, in a fluidized bed reactor with the solid reactant as a fine powder or else in a fixed bed reactor or also in a rotating reactor of the cement kiln type with the solid reactant in the porous granule form.

The process is preferably carried out semicontinuously in one or more tubular fixed bed reactors operating alternately, for example according to the technology for the treatment of gases with molecular sieves. After reaction, the solid reactant, partially or completely converted to calcium fluoride, is discharged from the reactor. The calcium fluoride, after optional separation of the unreacted calcium hydroxide, can be used as starting material in the manufacture of hydrofluoric acid.

The process according to the present invention can comprise the recycling of the unreacted reactants in the dehydrofluorination stage.

EXPERIMENTAL PART

Example 1

500 g of soda lime, Sigma Aldrich, with a particle size of 0.15 mm are charged to a tubular reactor with a length of 850 mm and a diameter of 43 mm heated to 140° C. by an electric resistance. A gas stream formed of 0.41 mol/h of HFC-236ea and 0.2 mol/h of an inert gas is passed through the reactor.

The gases exiting from the reactor pass through a reflux condenser at 10° C., in order to remove the water vapor, and are then condensed in a cold trap. After operating continuously for 80 min, the overall conversion of the HFC-236ea is 98% and the overall selectivity for HFO-1225ye is 99%.

Example 2

575 g of soda lime Sodasorb 4-8. REG HP (Grace), with a particle size of 3-6 mm and with a moisture content of 14-19% by weight, are charged to the same equipment as in example 1.

The reactant flow rate at the inlet of the reactor is 0.49 mol/h of HFC-236ea and 0.17 mol/h of an inert gas.

The tube is heated to 135° C. and the gases exiting from the tube are analyzed and collected in a cold trap.

A 100% conversion of the HFC-236ea is observed during the 100 min of operation.

The selectivity for HFO-1225ye is greater than 99%.

Example 3

690 g of soda lime Sodasorb 4-8 REG HP (Grace), with a particle size of 3-6 mm and with a moisture content of 14-19% by weight, are charged to the same equipment as in example 1.

The tube is heated to 120° C. and a flow rate of 0.5 mol/h of HFC-245eb is introduced.

The gases exiting from the tube are analyzed and collected in a cold trap.

After operating continuously for 4 h 35 min, the conversion of the HFC-245eb is 100% and the selectivity for 1234yf is 99%.

The invention claimed is:

1. A two-phase process for the continuous or semicontinuous manufacture of a (hydro)fluoroolefin compound, comprising contacting at least one linear or branched compound comprising from 2 to 6 carbon atoms, at least two fluorine atoms and at least one hydrogen atom, having at least one hydrogen atom and one fluorine atom situated on adjacent carbon atoms, with a solid reactant comprising calcium hydroxide at a temperature of between 100 and 170° C., wherein overall selectivity for the (hydro)fluoroolefin compound is greater than 80%.

2. The process as claimed in claim 1, characterized in that the (hydro)fluoroolefin comprises a compound of formula (I)

$$CF_3CY=CX_nH_p \qquad (I)$$

in which Y represents a hydrogen or halogen atom selected from the group consisting of fluorine, chlorine, bromine or iodine and X represents a halogen atom selected from the group consisting of fluorine, chlorine, bromine or iodine; and n and p are integers having the value zero, 1 or 2, provided that (n+p)=2, and the compound comprising from 2 to 6 carbon atoms comprises a compound of formula $CF_3CYRCR'X_nH_p$, in which R represents a fluorine atom when R' represents a hydrogen atom or R represents a hydrogen atom when R' represents a fluorine atom.

3. The process as claimed in claim 1, characterized in that the (hydro)fluoroolefin comprises a compound is of formula (Ia)

$$CF_3\text{—}CF\text{=}CHZ \qquad (Ia)$$

in which Z represents a hydrogen or fluorine atom, and the compound comprising from 2 to 6 carbon atoms comprises a compound of formula $CF_3CFRCHR'Z$, in which R represents a fluorine atom when R' represents a hydrogen atom or R represents a hydrogen atom when R' represents a fluorine atom.

4. The process as claimed in claim 1, characterized in that 2,3,3,3-tetrafluoropropene is obtained by contacting 1,2,3,3,3-pentafluoropropane with a solid reactant comprising calcium hydroxide.

5. The process as claimed in claim 1, characterized in that the solid reactant further comprises between 0.1 and 5% by weight of KOH.

6. The process as claimed in claim 1, characterized in that the solid reactant further comprises between 0.1 and 5% by weight of NaOH.

7. The process as claimed in claim 1, characterized in that the moisture content of the solid reactant is between 1 and 20% by weight.

8. The process as claimed in claim 1, characterized in that it is carried out at a pressure of between 1 and 10 bar absolute.

9. The process as claimed in claim 1, characterized in that the solid reactant is in the form of granules of from 1 to 10 mm.

10. The process as claimed in claim 1, characterized in that 1,2,3,3,3-pentafluoropropene is obtained by contacting 1,1,1,2,3,3-hexafluoropropane with a solid reactant comprising calcium hydroxide.

\* \* \* \* \*